(12) United States Patent
Shchekin et al.

(10) Patent No.: US 9,995,648 B2
(45) Date of Patent: Jun. 12, 2018

(54) OPTICAL MEASUREMENT SYSTEM AND METHOD FOR MEASURING CRITICAL DIMENSION OF NANOSTRUCTURE

(71) Applicant: SAMSUNG ELECTRONICS CO., LTD., Suwon-si (KR)

(72) Inventors: Alexey Shchekin, Moscow (RU); Maksim Riabko, Moscow (RU); Sergey Koptyaev, Moscow (RU); Anton Medvedev, Moscow (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 133 days.

(21) Appl. No.: 14/850,425

(22) Filed: Sep. 10, 2015

(65) Prior Publication Data

US 2016/0131472 A1 May 12, 2016

(30) Foreign Application Priority Data

Nov. 10, 2014 (RU) .................................. 2014145185
Jun. 22, 2015 (KR) ......................... 10-2015-0088724

(51) Int. Cl.
*G01B 11/02* (2006.01)
*G01N 21/95* (2006.01)
(Continued)

(52) U.S. Cl.
CPC ...... *G01M 11/005* (2013.01); *G01M 11/0271* (2013.01); *G01N 21/9501* (2013.01); *G03F 7/70625* (2013.01); *G01B 2210/56* (2013.01)

(58) Field of Classification Search
CPC ........... G01M 11/005; G01M 11/0242; G01M 11/0257; G01M 11/0271; G01N 21/9501;
(Continued)

(56) References Cited

U.S. PATENT DOCUMENTS 4,818,110 A * 4/1989 Davidson ............. G01B 11/024
356/512
6,977,714 B2 12/2005 Finders
(Continued)

FOREIGN PATENT DOCUMENTS

CN 102944983 A 2/2013
CN 103268009 A 8/2013
(Continued)

OTHER PUBLICATIONS

Ray J. Hoobler and Ebru Apak, "Optical critical dimension (OCD) measurements for profile monitoring and control: applications for mask inspection and fabrication," Proc. SPIE 5256, 23rd Annual BACUS Symposium on Photomask Technology, (Dec. 17, 2003); doi: 10.1117/12.517931; pp. 638-645.
(Continued)

*Primary Examiner* — Michael A Lyons
(74) *Attorney, Agent, or Firm* — Sughrue Mion, PLLC

(57) ABSTRACT

Provided is an optical measurement system. The optical measurement system includes: an optical module which includes an optical system and which is configured to illuminate a sample and register a defocused image of a nanostructured surface of the sample, an optical system parameter control module configured to set optical parameters of the optical system, an optical transfer function (OTF) measurement module configured to measure an OTF, a defocused image calculation module configured to calculate the defocused image based on the measured OTF and the optical parameters, and a critical dimension (CD) evaluation module configured to compare the registered defocused image with the calculated defocused image of the nanostructured surface of the sample and to output a CD value of the nanostructured surface.

17 Claims, 9 Drawing Sheets

(51) Int. Cl.
*G01M 11/00* (2006.01)
*G01M 11/02* (2006.01)
*G03F 7/20* (2006.01)

(58) Field of Classification Search
CPC .............. G01N 21/956; G03F 7/70625; G01B 9/02029; G01B 9/0203; G01B 9/02063; G01B 9/0209; G01B 11/02; G01B 2210/56
See application file for complete search history.

(56) References Cited

U.S. PATENT DOCUMENTS

| | | | |
|---|---|---|---|
| 8,089,612 B2 | 1/2012 | Matsumoto et al. | |
| 8,653,454 B2 | 2/2014 | Chen et al. | |
| 9,322,640 B2* | 4/2016 | Koptyaev | G01B 11/02 |
| 9,360,662 B2* | 6/2016 | Koptyaev | G02B 21/365 |
| 9,400,254 B2* | 7/2016 | Shcherbakov | |
| 2002/0145741 A1 | 10/2002 | Kosuge et al. | |
| 2006/0172207 A1 | 8/2006 | Asaba et al. | |
| 2012/0120485 A1* | 5/2012 | Ootomo | G01B 9/04 359/370 |
| 2013/0107030 A1 | 5/2013 | Koptyaev et al. | |
| 2014/0240697 A1* | 8/2014 | Xiang | G03F 7/706 356/121 |
| 2015/0345934 A1* | 12/2015 | Shafir | G01N 21/956 356/364 |

FOREIGN PATENT DOCUMENTS

| | | |
|---|---|---|
| DE | 102010037738 A1 | 4/2011 |
| EP | 2 587 313 A2 | 5/2013 |

OTHER PUBLICATIONS

Ravikiran Attota, Richard Silver, Bryan M. Barnes, "Optical Through-Focus Technique that Differentiates Small Changes in Line Width, Line Height and Sidewall Angle for CD, Overlay, and Defect Metrology Applications"; Proc. SPIE vol. 6922, 69220E, (2008); pp. 1-12.

Ryabko, M.V.; Koptyaev, S.N.; Shcherbakov, A.V.; Lantsov, A.D.; Oh, S.Y.; "Method for optical inspection of nanoscale objects based upon analysis of their defocused images and features of its practical implementation"; Optics Express, vol. 21, Issue 21, pp. 24483-24489 (Oct. 2013).

H. H. Hopkins, "On the diffraction theory of optical images"; Proc. R. Soc. Lond. A, (1953) vol. 217 No. 1130, pp. 408-432.

Colin J. R. Sheppard, "Defocused transfer function for a partially coherent microscope and application to phase retrieval"; J. Opt. Soc. Am. A/vol. 21, No. 5, May 2004, pp. 828-831.

J.A. Nelder and R. Mead, "A simplex method for function minimization"; Computer Journal, 1965, vol. 7, pp. 308-313.

Hooke, R.; Jeeves, T.A. (1961); "'Direct Search' Solution of Numerical and Statistical Problems"; Journal of the Association for Computing Machinery (ACM) 8 (2): pp. 212-229; doi :10.1145/321062.321069.

M. G. Moharam, Drew A. Pommet, and Eric B. Grann, "Stable implementation of the rigorous coupled-wave analysis for surface-relief gratings: enhanced transmittance matrix approach", J. Opt. Soc. Am. A, vol. 12, No. 5, pp. 1077-1086, May 1995.

K. Umashankar, A. Taflove, "A Novel Method to Analyze Electromagnetic Scattering of Complex Objects", IEEE (1982), vol. EMC-24, No. 4, Nov. 1982, pp. 397-405.

Attota, R., Silver, R.M., and Potzick, J., "Optical illumination and critical dimension analysis using the through-focus focus metric method" Proc. SPIE, 6289, p. 62890Q-1-10 (Sep. 5, 2006).

\* cited by examiner

OPTICAL MEASUREMENT SYSTEM AND METHOD FOR MEASURING CRITICAL DIMENSION OF NANOSTRUCTURE

CROSS-REFERENCE TO RELATED APPLICATIONS

This application claims priority from Russian Patent Application No. 2014145185, filed on Nov. 10, 2014 in the Russian Patent Office and Korean Patent Application No. 10-2015-0088724, filed on Jun. 22, 2015 in the Korean Intellectual Property Office, the disclosures of which are incorporated herein by reference in their respective entireties.

BACKGROUND

1. Field

Exemplary embodiments relate to a technique for measuring a nanoscale object, and more particularly, to an optical measurement system and a method for determining a critical dimension (CD) of a nanoscale object.

2. Description of the Related Art

Recently, there has been a distinct tendency toward decreasing a critical dimension (CD) of a manufactured structure in micro lithography technology for semiconductor chip manufacturing. The CD is a measure of a nanostructure that is a test target and has a value in the range of about several tens of nanometers. At present, it is possible to obtain a CD of about 30 nm, and it is expected to reduce the CD to about 20 nm in the near future.

For semiconductor structures having very small critical dimensions (CDs), demands for a highly accurate and reliable measurement system and a fast and low-cost measurement process have increased. A conventional measurement method using a scanning electron microscope (SEM) and an atomic force microscope (AFM) has problems of relatively low speed and relatively high cost when a chip is tested using a well-known topology having a dimension slightly different from a required CD value for a semiconductor structure. For this type of measurement, optical methods based on ellipsometry and scatterometry have been developed. In particular, a well-known optical critical dimension (OCD) method is used to identify a semiconductor structure having a smaller CD than a Rayleigh limit.

Non-periodical isolated objects may be analyzed by using through-focus scanning optical microscopy (TSOM) based on analyzing a non-contrast defocused image of a registered object via a microscope optical system while scanning the object along an optical axis.

SUMMARY

Provided is an optical measurement system and a method for measuring a CD of a nanostructure by applying an optical transfer function (OTF) in CD measurement via defocused image analysis.

Additional aspects will be set forth in part in the description which follows and, in part, will be apparent from the description, or may be learned by practice of the presented exemplary embodiments.

According to an aspect of an exemplary embodiment, an optical measurement system includes an optical module including an optical system and configured to illuminate a sample and to register a defocused image of a nanostructured surface of the sample, an optical system parameter control module configured to set at least one optical parameter of the optical system, an optical transfer function (OTF) measurement module configured to measure an OTF, a defocused image calculation module configured to calculate the defocused image based on the measured OTF and the at least one optical parameter, and a critical dimension (CD) evaluation module configured to compare the registered defocused image with the calculated defocused image and to output a CD value of the nanostructured surface of the sample. The OTF measurement module may be further configured to analyze interferograms that correspond to an illumination light aberrated by the optical measurement system and a reference light.

The OTF measurement module may be further configured to measure the OTF based on the registered defocused image of the nanostructured surface of the sample.

The optical system parameter control module may be further configured to set at least one parameter of the optical measurement system and at least one parameter of the OTF measurement module, in which the at least one parameter of the optical measurement system includes at least one from among a spectrum and a polarization of a light source, a numerical aperture of an objective lens, a full range and a step size of defocusing of the sample, and a magnification of the optical measurement system.

The defocused image calculation module may be further configured to calculate the image by using at least one of a Rigorous coupled-wave analysis (RCWA) method, a finite-difference time-domain (FDTD) method, a finite elements method (FEM), and a scattering matrix.

The CD evaluation module may be further configured to find a defocused image that matches a registered defocused image from a defocused image library calculated in advance for different CD values.

When an accuracy of the output CD value of the nanostructured surface of the sample fails to satisfy a predetermined minimum accuracy, the defocused image calculation module may be further configured to repeat an image calculation by using a smaller CD step size until the accuracy of the CD value satisfies the predetermined minimum accuracy.

The OTF measurement module may be further configured to measure a phase factor of the OTF and to separately measure an amplitude factor of the OTF.

According to an aspect of an exemplary embodiment, an optical measurement method includes setting at least one optical parameter of an optical measurement system, measuring an optical transfer function (OTF) of the optical measurement system, registering a defocused image of a nanostructured surface of a sample at at least one sample position along an optical axis of an optical system based on the optical measurement system, calculating a defocused image based on the measured OTF in a preset CD value range, and evaluating an accuracy of a CD of the nanostructured surface of the sample by comparing the registered defocused image with the calculated defocused image.

The measuring of the OTF may include analyzing interferograms that correspond to an illumination light aberrated by the optical measurement system and a reference light.

The measuring of the OTF may include measuring the registered defocused image of the nanostructured surface of the sample.

The at least one parameter of the optical measurement system may include at least one from among a spectrum and a polarization of a light source, a numerical aperture of an objective lens, a full range and a step size of defocusing of the sample, and a magnification of the optical measurement system.

The evaluating the accuracy of the CD may be performed based on an arithmetic difference between the registered defocused image and the calculated defocused image for measuring a CD value that corresponds to the nanostructured surface of the sample.

The evaluating the accuracy of the CD may be performed based on a focus metric function for measuring a CD value that corresponds to the nanostructured surface of the sample.

The evaluating the accuracy of the CD may include finding a defocused image that matches a registered defocused image from a defocused image library calculated in advance for different CD values.

When an accuracy of the output CD value of the nanostructured surface of the sample fails to satisfy a predetermined minimum accuracy, the calculating the defocused image may be repeated by using a smaller CD step size, and the evaluating the accuracy of the CD may be repeated until the accuracy of the CD value satisfies the predetermined minimum accuracy.

The measuring the OTF may include measuring a phase factor of the OTF and separately measuring an amplitude factor of the OTF

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
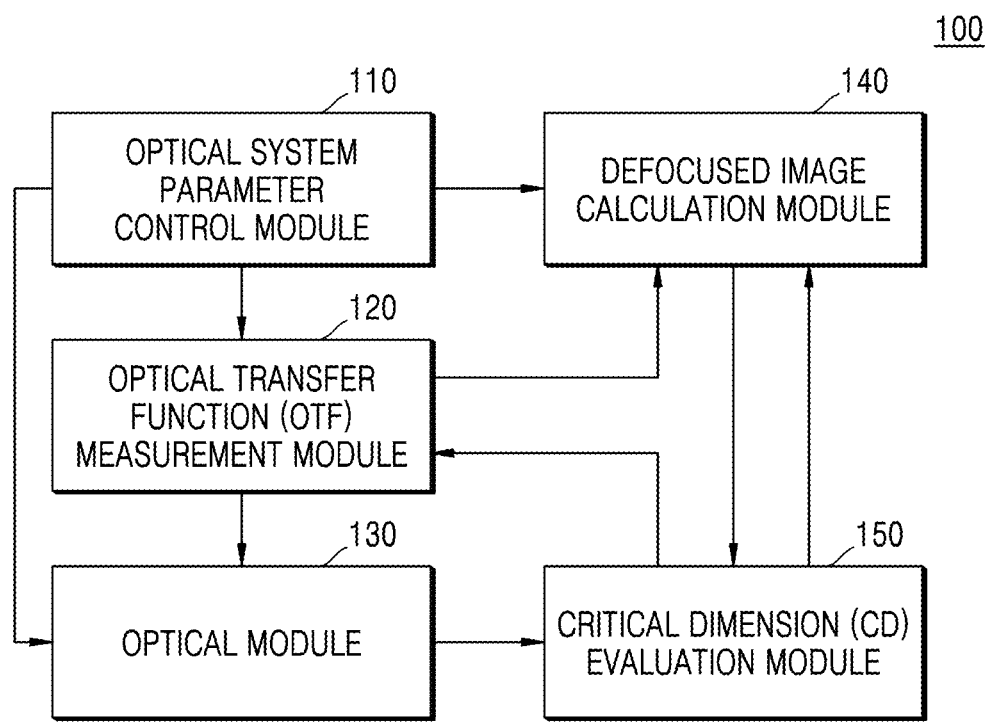
FIG. 1 is a block diagram illustrating a schematic structure of an optical measurement system, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Throughout the specification, when it is described that an element is "connected" to another element, it may be "electrically connected" to the other element having another element therebetween as well as "directly connected" to the other element. Further, when it is described that a part "includes" an element, it means that the part may further include another element, rather than exclude another element, unless specifically expressed otherwise.

Hereinafter, the exemplary embodiments will be described in detail with reference to the accompanying drawings.

FIG. 1 is a block diagram illustrating a schematic structure of an optical measurement system 100, according to an exemplary embodiment. Referring to FIG. 1, the optical measurement system 100 may include a combination of hardware and software. The hardware may include an optical system parameter control module 110, an optical transfer function (OTF) measurement module 120, and an optical module 130, and the software may include a defocused image calculation module 140 and a critical dimension (CD) evaluation module 150.

The optical module 130 records or registers an image of a nanostructured surface of a sample, which image is obtained via a microscope optical system. Herein, the registered image includes a complex overlay of diffraction patterns, and analysis may be carried out in order to extract an unknown CD from the registered image.

The OTF measurement module 120 measures an OTF of the optical measurement system 100.

The optical system parameter control module 110 sets and outputs one or more optical parameters of the microscope optical system and transmits the measured optical parameters to the defocused image calculation module 140.

The defocused image calculation module 140 calculates a defocused image based on of the OTF measured in a predetermined CD variation range and the optical parameters measured by the optical system parameter control module 110.

The CD evaluation module 150 compares the calculated image with the measured image (i.e., the recorded or registered image). This module for comparing the measured image of the nanostructured surface of the sample with the calculated image is of particular importance in the measurement system 100. For comparison, the measured image obtained by the optical module 130 and the calculated image obtained by the defocused image calculation module 140 may be transmitted to be input to the CD evaluation module 150. As a comparison result, an optimal estimate of the measured CD value and/or a CD value variation range which is adjusted to be narrower may be derived.

The calculation in the defocused image calculation module 140 and the comparison in the CD evaluation module 150 may be repeated while changing a CD value, until the calculated image matches the measured image. The CD value that is used when the calculated image matches the measured image may be the best estimate of the CD value of the nanostructured surface of the sample.

The optical measurement system 100, according to an exemplary embodiment, may be different from the aforementioned through-focus scanning optical microscopy (TSOM) scheme as the optical measurement system 100 uses the OTF measurement module 120. In particular, the OTF measurement module 120 may be used to determine an optical system pupil function and illumination conditions via measurement of a light source distribution in a back focal plane, by applying Equation (1), which is expressible as follows:

$$P(r,\theta) = A(r,\theta)e^{i\varphi(r,\theta)} \quad (1)$$

$$E = E(r,\theta)$$

where (r,θ) represent polar coordinates over the optical system pupil, E(r,θ) represents an illumination field, P(r,θ) represents an optical system pupil function forming an amplitude part A(r,θ) and a phase part φ(r,θ). The optical system pupil function, together with the illumination conditions, may define the OTF as a bilinear form of spatial frequency components. For weak objects, the bilinear form may be simplified according to Equation (2), which is expressible as follows:

$$\mathrm{OTF} = (|E|^2 P^*) \otimes P \quad (2)$$

where E, P represent the aforementioned illumination field and optical system pupil function, and the OTF may be an OTF for a given optical system.

An amplitude factor A(r,θ) in Equation (1) may characterize optical system transmissions at different points of the pupil, and φ(r,θ) may denote an additional phase caused by optical system aberrations and misalignment of the optical elements.

After the optical measurement system 100 is calibrated based on the illumination conditions and the OTF, a defocused image of a sample nanostructured surface may be acquired. Under the same conditions, defocused images may be calculated by the defocused image calculation module 140 at different CD values, thus forming a TSOM library. The range of usable CDs should cover an actually possible CD range, and a CD step size should be at least less than a maximum CD step size that corresponds to the required CD accuracy.

A comparison between the registered defocused image and the calculated defocused image may be performed by the CD evaluation module 150. If the required accuracy is not achieved for all CD values from the library, the library calculation may be repeated by using a smaller step size, and then the CD evaluation process may be repeated until the required accuracy is achieved.

The foregoing process may derive the best estimate of the CD value of the nanostructured surface of the sample.

Figure 2:
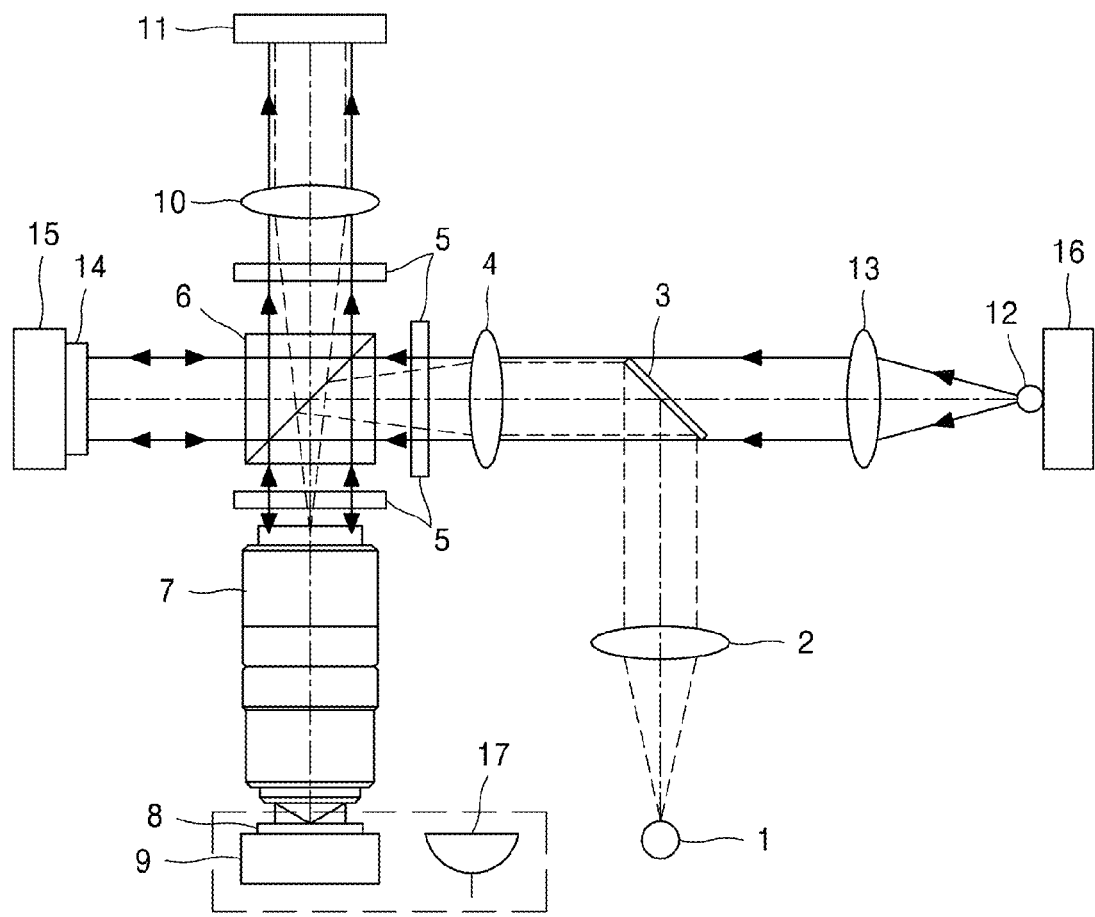
FIG. 2 illustrates an exemplary optical arrangement of an optical module of an optical measurement system, according to an exemplary embodiment.

FIG. 2 illustrates an exemplary optical arrangement of an optical module used in an optical measurement system, according to an exemplary embodiment.

Referring to FIGS. 1 and 2, the optical module 130 may form a microscope optical system which is configured to obtain a defocused image of a nanostructured surface of a sample 8 that is a test target. The optical module 130 may adopt, for example, a microscope optical system configuration which employs a Koehler illumination method while operating in a bright field mode.

The optical module 130 may include a light source 1, lenses 2 and 4, a mirror 3, a polarizer 5, a beam splitter 6, an objective lens 7, a precision mechanical stage 9, a tube lens 10, and an image sensor 11. The optical module 130 receives experimental conditions specified by the optical system parameter control module 110, and registers a defocused image of the sample 8. The optical module 130 transmits defocused images obtained experimentally to the CD evaluation module 150.

The light source 1 provides an illumination light for obtaining an image of the sample 8. An illumination spectrum which includes a light in a predetermined wavelength band may be provided to the sample 8, and the illumination spectrum may be implemented by the light source 1.

The beam splitter 6 splits a light path in order to direct the light from the light source toward the sample 8 and to direct the light reflected and scattered from the sample 8 toward the image sensor 11. The beam splitter 6 may include a polarization beam splitter.

The image sensor 11 converts an optical image into an electric signal and may include, for example, a charge coupled device (CCD).

The precision mechanical stage 9 is designed to scan the sample 8 along at least one axis at a nanometer-scale precision.

The tube lens 10 may be disposed between the beam splitter 6 and the image sensor 11.

Referring to FIGS. 1 and 2, the optical system parameter control module 110 sets one or more parameters in order to form an optical system for registering an image of a nanostructured surface of a sample. For example, the optical system parameter control module 110 may set and output parameters which form the optical system illustrated in FIG. 2. The optical system parameters may be measured and/or changed. The optical system parameter control module 110 may include the lenses 2 and 4 and the polarizer 5.

According to the set optical system parameters, the optical module 130 may register a nanostructured surface image. To enable the defocused image calculation module 140 to calculate the nanostructured surface image, the optical system parameters may be transmitted to the defocused image calculation module 140.

The optical system parameters are also transmitted to the OTF measurement module 120 that measures an OTF under the set optical system parameter conditions. The OTF measurement module 120 specifies defocused images with various CDs calculated by the defocused image calculation module 140 based on the required CD evaluation accuracy.

Referring to FIGS. 1 and 2, the OTF module 120 may include the polarizer 5, the beam splitter 6, the objective lens 7, the sample 8, precision mechanical stages 9, 15, and 16, the image sensor 11, a light source 12, a lens 13, a reference mirror 14, and a photodetector 17. The OTF measurement module 120 measures the OTF under conditions specified by the optical system parameter control module 110, and transmits the measured OTF to the defocused image calculation module 140.

The OTF measurement module 120 measures a phase factor of the OTF, and separately measures an amplitude factor of the OTF. The phase factor φ(r,θ) may be measured by, for example, a Twyman-Green interferometer. For measurement of the phase factor, the mirror 3 and the lenses 4 and 10 may be removed. The beam from the light source 12 is collimated by the lens 13 and illuminates the sample 8. The beam may be split by the beam splitter 6 and is incident into two channels. In the first channel, the beam traverses the objective lens 7 and is affected by a phase change caused by objective lens aberrations and sample defocusing. In the second channel, the beam is reflected from the reference mirror 14 which is placed on the precision mechanical stage 15. The precision mechanical stage 15 may adjust the position of the reference mirror 14 along an optical axis. The two beams are sensed by the image sensor 11 and generate an interference pattern. An intensity distribution in the interference pattern may include information about a phase distribution over an optical system pupil. In the absence of aberrations and sample defocusing, the interference pattern may have a uniform form. Conversely, any uniformity may function as a sign of an existence of aberrations in the optical system.

To increase the accuracy of the phase measurement, a plurality of (i.e., at least three) interference patterns are collected at different positions of the reference mirror 14 as adjusted by the mechanical stage 15. The adjusting range of the reference mirror 14 may be in the range of a wavelength of the light source 12 used in the optical system. The following phase retrieval is performed, for example, as a part of a phase-stepping interferometry method, by the application of Equation (3), which is expressible as shown below. The phase-stepping interferometry method is based on an assumption that the intensity of an $n^{th}$ interference pattern collected at a position $z_n$ of the reference mirror 14 is defined by three parameters $I_0$, $\gamma_0$, and $\varphi$.

$$I_n(r,\theta)=I_0(r,\theta)(1+\gamma_0(r,\theta)\cos(\varphi(r,\theta)+\alpha_n)) \qquad (3)$$

where $\varphi(r,\theta)$ represents a phase spatial distribution over an optical system pupil to be measured; $I_0, \gamma_0$ represent parameters defining the intensity and contrast of the interference pattern; and $$\alpha_n = \frac{4\pi}{\lambda} z_n$$

represents a phase added due to movement of the reference mirror 14 to the position $z_n$. Since n interference patterns are given, Equation (3) results in an overdefined system of equations that may be solved by using a least-square method to find the phase distribution $\varphi(r,\theta)$, via an application of Equation (4), which is expressible as follows:

$$\begin{pmatrix} \cos\alpha_2 - \cos\alpha_1 & \sin\alpha_1 - \sin\alpha_2 \\ \cos\alpha_3 - \cos\alpha_2 & \sin\alpha_2 - \sin\alpha_3 \\ \ldots & \ldots \end{pmatrix} \begin{pmatrix} I_0\gamma_0\cos\varphi \\ I_0\gamma_0\sin\varphi \end{pmatrix} = \begin{pmatrix} I_2 - I_1 \\ I_3 - I_2 \\ \ldots \end{pmatrix} \qquad (4)$$

The accuracy of the phase measurement may be limited by one or more of the accuracy and reproducibility of a measured interference pattern stipulated by digital camera noises, mechanical vibration of an optical system, and the accuracy of a sample and a reference mirror position.

Figure 3A:
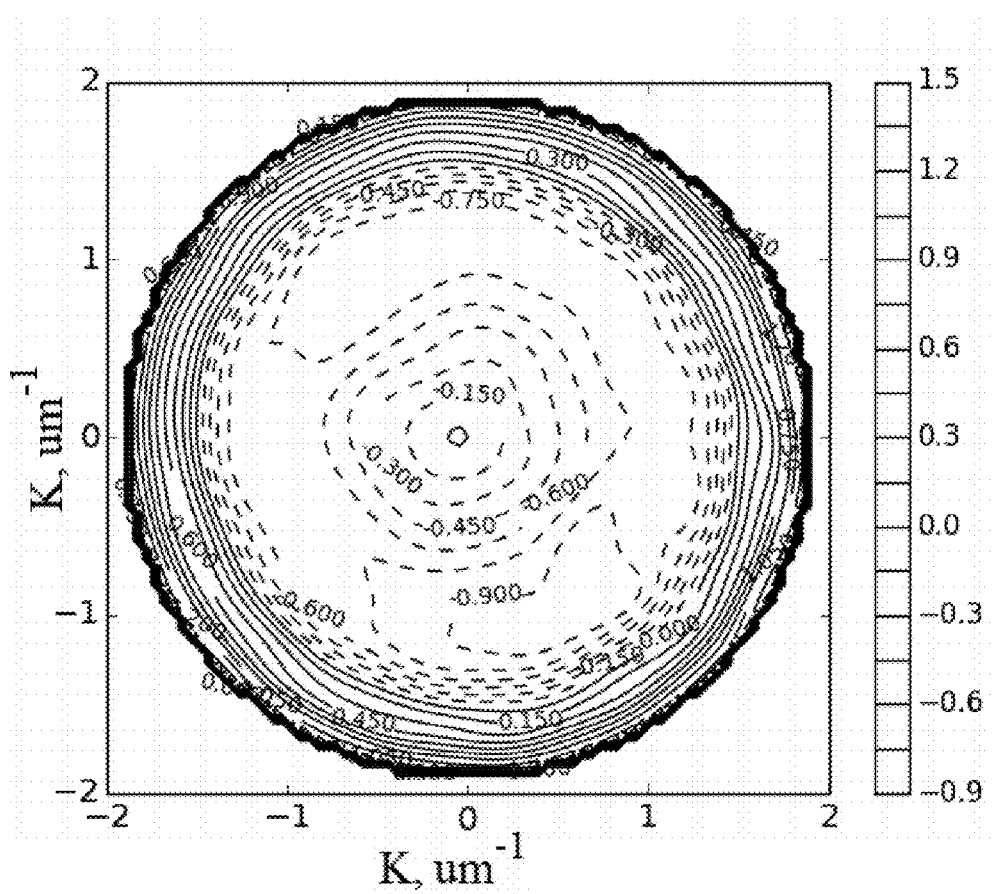
FIG. 3A illustrates a phase factor distribution of a pupil function.

The influence of noise on the phase factor $\varphi(r,\theta)$ may be reduced by fitting the raw measured phase factor $\varphi(r,\theta)$ by a two-dimensional Zernike polynomial. This process may facilitate an elimination of periodical noises of the phase factor $\varphi(r,\theta)$, which are not related to optical system aberrations caused by light interference on flat optical elements. The phase distribution fitted by the typical Zernike polynomials in the optical system pupil function is shown in FIG. 3A.

Figure 3B:
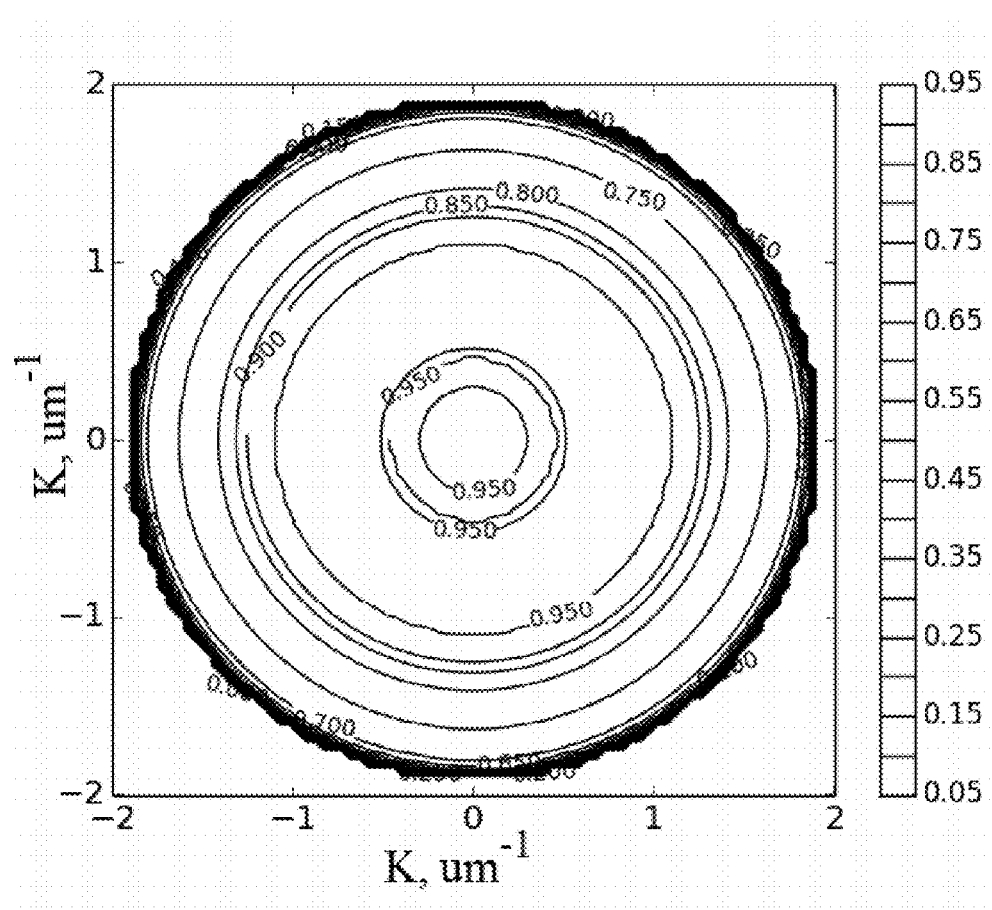
FIG. 3B illustrates an amplitude factor distribution of a pupil function.

When the amplitude factor $A(r,\theta)$ of the optical pupil function is measured, the sample 8 and the precision mechanical stage 9 may be replaced by the photodetector 17. The light source 12, which is provided in a scanning mechanical stage 16, is used for illumination. Movement of the light source 12 on an x-y plane causes a shift of an image in the back focal plane. In addition, the shift of the image makes it possible to measure a transmission factor of the objective lens as a function of pupil coordinates $(r,\theta)$. This function may be the same as the amplitude factor $A(r,\theta)$ of the optical pupil function. The amplitude factor distribution of the pupil function is shown in FIG. 3B.

The illumination conditions are defined by an illumination source field distribution $E(r,\theta)$ distribution in the back focal plane of the objective lens 7. This distribution is measured at the reproducibly removed lens 4, and uses the same light source 1 as that used to collect defocused images. Under these conditions, the illumination source forms an image on the surface of the sample 8 by means of the lens 2 and the objective lens 7, and forms an image on the image sensor 11 by means of the objective lens 7 and the tube lens 10. The intensity distribution measured by the image sensor 11 may be a scaled intensity spatial distribution of the light source $I(r,\theta)$ over the pupil. In addition, by using the measured intensity distribution, the illumination field distribution $E(r,\theta)$ may be calculated.

The functions $P(r,\theta)$ and $E(r,\theta)$ measured above may define the OTF of the optical measurement system according to Equation (2).

According to another exemplary embodiment, the optical OTF measurement module 120 may be executed by a software algorithm which is integrated with the defocused image calculation module 140. Measurement of the OTF may be based on analysis of a defocused image of a well-known calibrated sample, and also based on analysis of the amplitude and phase factors in the known illumination conditions. Input parameters may be registered defocused images of calibrated samples. A $k^{th}$ iteration defocused image calculation may be performed by using a $k^{th}$ approximation of a pupil function $P_k(r,\theta)$. An output difference parameter $D_k$ may be defined based on an absolute value of a difference between a calculated defocused image and a registered defocused image. A transition to the next iteration algorithm may entail a modification of $P_k(r,\theta)$ with an intent to minimize the parameter $D_k$. This procedure may be carried out by, for example, multi-dimensional optimization algorithms. As a result, $P_{k+1}(r,\theta)$ may be used for the next $(k+1)^{th}$ iteration algorithm for defocused image calculation. The above-described process may be repeated until the calculated defocused image and the registered defocused image match within a preset accuracy range. The above-described algorithm may use, but is not limited to, programs such as Microsoft Visual Studio, Fortran, Borland C++ Builder, Matlab, Mathematica, Labview, and so forth.

Defocused images of a calculated sample and a comparison with an experimentally registered defocused image may require consideration of all parameters of the optical measurement system 100 which affect illumination and image registration conditions. To this end, all parameters should be measured in advance and transmitted to the defocused image calculation module 140, which takes the measured OTF into account. The above-mentioned parameters may include any one or more of the spectrum and polarization of the illumination light source, a numerical aperture of the objective lens 7, a full range and a step size of the sample defocusing, and a magnification of the optical measurement system 100. Equipment used for the foregoing purpose may be included in the optical system parameter control module 110.

The defocused image calculation module 140, while accounting for the measured OTF, may be configured to calculate an image by using, for example, any of a Rigorous coupled-wave analysis (RCWA) method and a finite-difference time-domain (FDTD) method. The RCWA method and the FDTD method make it possible to obtain a scattered field distribution $E(x,y)$ and a corresponding spatial spectrum $S(k_{xy})$ in the sample plane. The defocused image may be obtained from the spatial spectrum $S(k_{xy})$ calculated by the following process:

i) Low-pass filtering according to the numerical aperture of the objective lens 7 and an illumination wavelength, via application of Equation (5), which is expressible as follows:

$$S_1(k_{xy}) = \begin{cases} S(k_{xy}), & k_{xy} \le 2\pi \frac{NA}{\lambda} \\ 0, & k_{xy} > 2\pi \frac{NA}{\lambda} \end{cases}, \quad (5)$$

where λ,NA respectively represent the illumination wavelength and the numerical aperture of the objective lens 7, $k_{xy}$ represents a wave vector on an x-y plane which is perpendicular to an optical axis z, S represents an FDTD scattered field spatial spectrum amplitude, and $S_1$ represents a filtered spectrum.

ii) Spatial spectrum filtering taking a pupil function and sample defocusing into account by applying Equation (6), which is expressible as follows:

$$S_2(k_{xy}, Z) = P(k_{xy}) \cdot Def(k_{xy}, Z) \cdot S_1(k_{xy}), \quad (6)$$

$$Def(k_{xy}, Z) = \exp\left(iZ \cdot \sqrt{\left(\frac{2\pi}{\lambda}\right)^2 - k_{xy}^2}\right),$$

where $S_2$ represents a defocused spatial spectrum, and $P(k_{xy})$ represents a measured pupil function.

iii) Inverse Fourier transformation which transforms from a spatial spectrum into an image space by application of Equation (7), which is expressible as follows:

$$S_2(k_{xy}, Z) \to E_2(x, y, Z) \quad (7)$$

where $E_2$ represents a defocused image field.

iv) Calculating an image intensity, that is, summing all plane waves that form an illumination spatial spectrum, via application of Equation (8), which is expressible as follows:

$$I_2(x, y, Z) = \sum_{NAill} |E_2(x, y, Z)|^2, \quad (8)$$

where $I_2$ represents a defocused image intensity.

Input parameters may include any one or more of a measured OTF, optical parameters defining the illumination and defocused image registration conditions, and a CD variation range determining a defocused image library. The CD variation range is already known and is defined by a nanostructure manufacturing process. A narrower CD variation range may also be selected.

The CD evaluation module 150 compares an actually registered defocused image with images included in a library in order to determine the CD. The CD evaluation module 150 may select a CD value that corresponds to the best match between the experimentally registered defocused image and the calculated defocused image. If a difference between images is larger than a preset minimum accuracy, defocused image calculation may be repeated by using a smaller CD step size and in a narrower CD range. The CD evaluation process may be repeated until the difference between the images falls within the required accuracy range.

A comparison between the registered defocused image and the defocused image calculated from the library may be performed in any of various ways. In any case, the comparison may result in an absolute value that defines how closely the registered defocused image matches the calculated image obtained from the library.

A representative method for comparing the registered defocused image with the calculated defocused image may measure an average value $M_{CD}$ of an absolute difference by applying Equation (9), which is expressible as follows:

$$M_{CD} = \frac{\sum_{xy} |I_{measured} - I_{CD}|}{N_{xy}}, \quad (9)$$

where $I_{measured}$, $I_{CD}$ respectively represent measured and calculated defocused images for a particular CD value, and $N_{xy}$ represents the number of pixels of a defocused image.

Figure 3C:
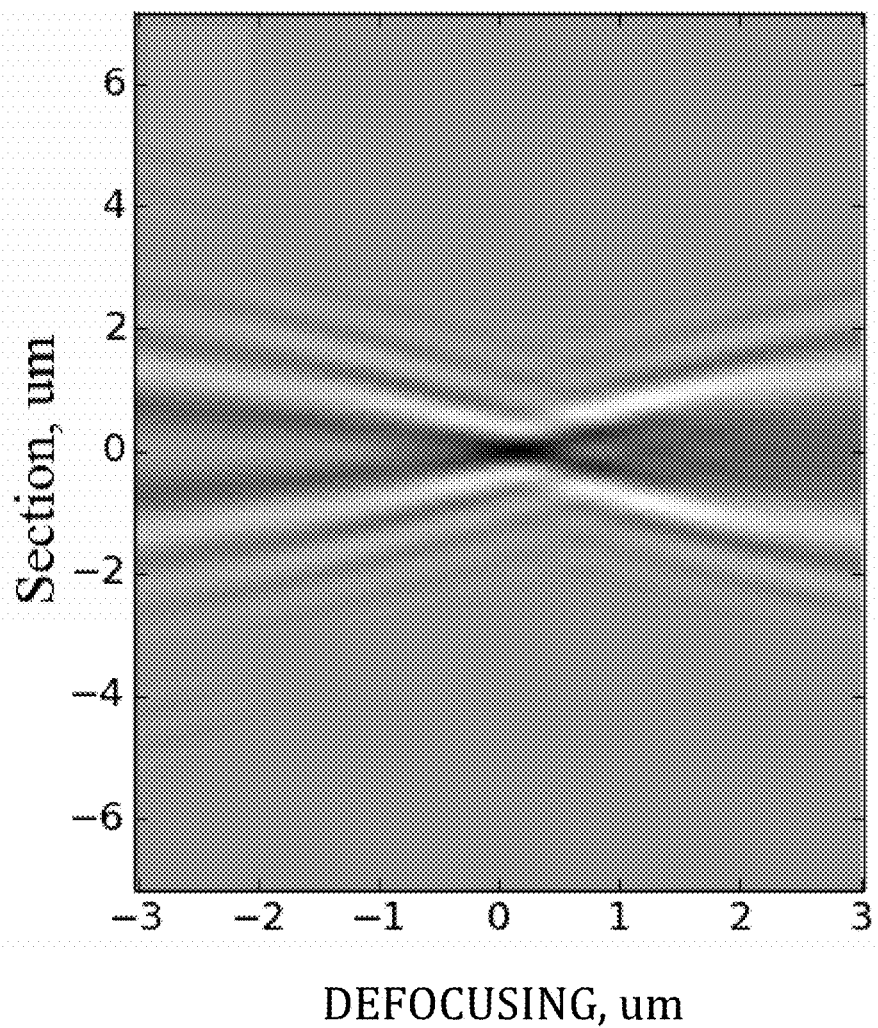
FIG. 3C illustrates a registered defocused image of a 40×50 nm silicon nano-rod on a silicon plane.
Figure 3D:
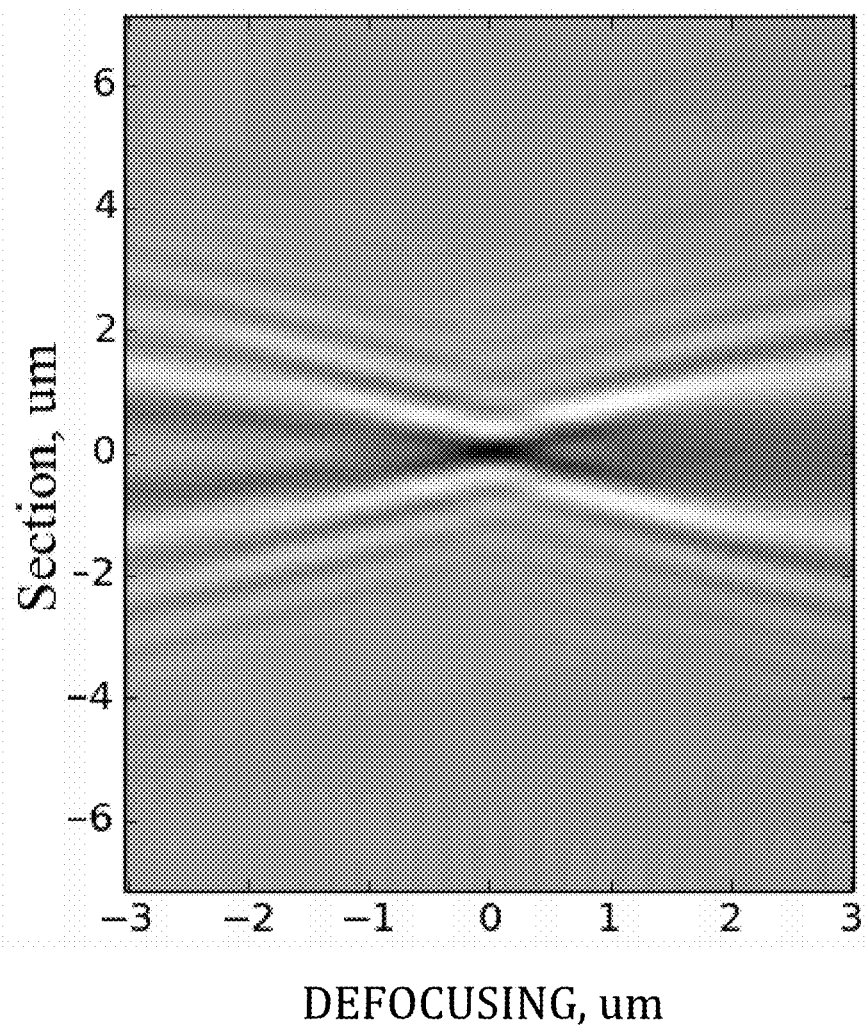
FIG. 3D illustrates a calculated defocused image of a 40×50 nm silicon nano-rod on a silicon plane.
Figure 3E:
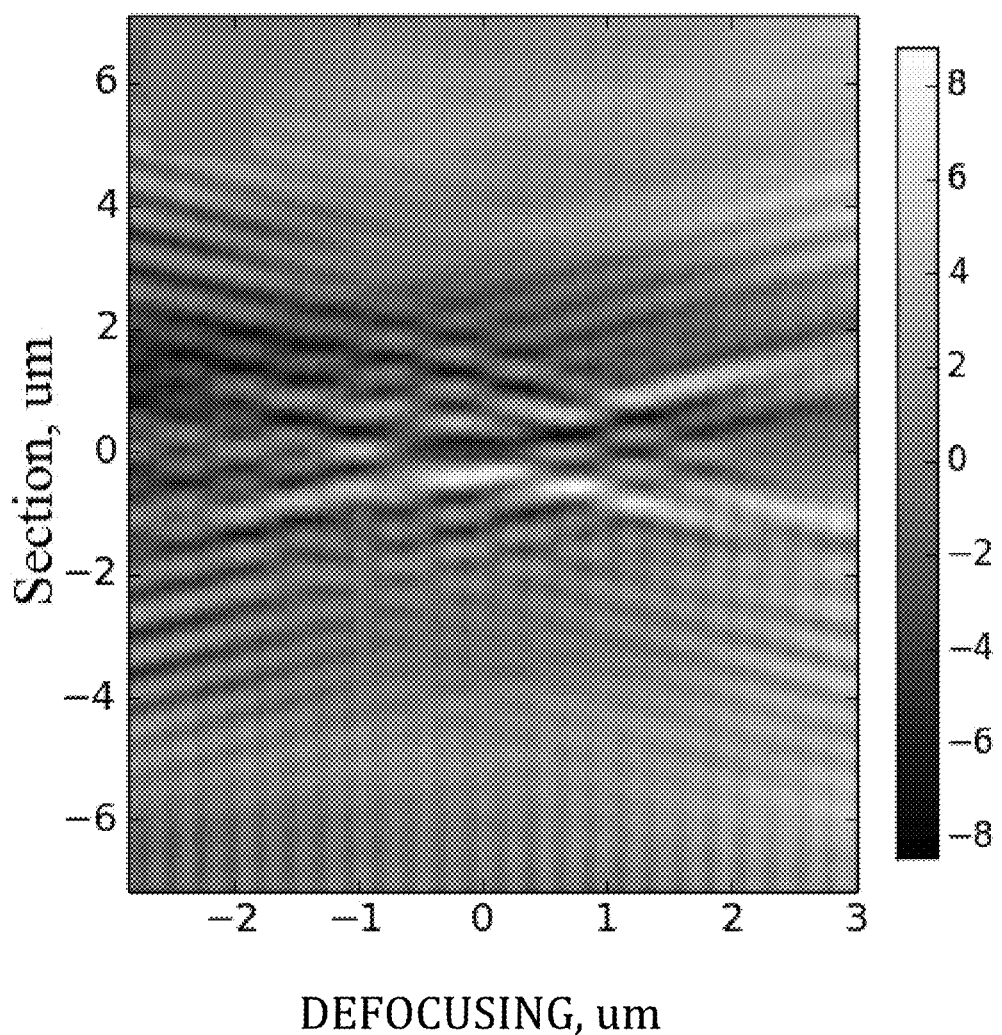
FIG. 3E shows a difference between a registered defocused image and a calculated defocused image.

Zero $M_{CD}$ means matching between the two images for a given CD value. FIGS. 3C and 3D illustrate registered and calculated defocused images of 40×50 nm silicon nano-rods on a silicon flat surface. FIG. 3E shows a difference $M_{CD}$ between the registered defocused image and the calculated defocused image.

Figure 3F:
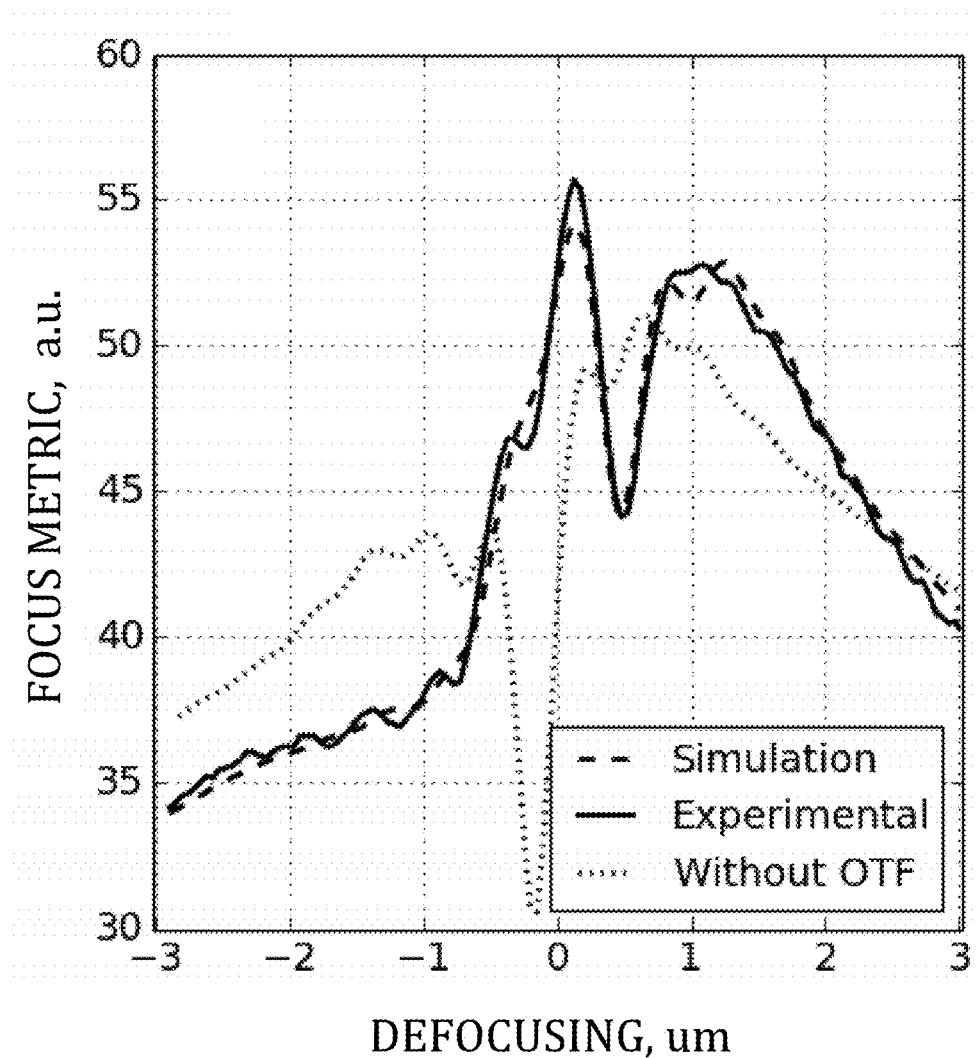
FIG. 3F shows a "focus metric" curve extracted from images of FIGS. 3C and 3D, a curve based on a measured optical transfer function, and a curve not based on an optical transfer function.

FIG. 3F shows a "focus metric" curve extracted from the images of FIGS. 3C and 3D, a curve taking the measured OTF into account, and a curve not taking the OTF into account.

A focus metric parameter characterizes an image contrast at a given defocusing degree, and may include a standard deviation that is calculated from a digital image which indicates a data array expressed as below. A parameter M(I(x,y,Z)) which varies based on a topology of an object and a degree of defocusing may be provided in correspondence to each defocused image I(x,y,Z), in accordance with Equation (10), which is expressible as shown below. This parameter may indicate an image contrast for a predetermined defocusing degree. In particular, this parameter may include a standard deviation that is calculated from a digital image which indicates a data array.

$$M(Z) = STD_{x,y}(I(x, y, Z)) = \sqrt{\frac{1}{N_{x,y}} \sum_{x,y} (I(x, y, Z) - \bar{I}(Z))^2}, \quad (10)$$

$$\bar{I}(Z) = \frac{1}{N_{x,y}} \cdot \sum_{x,y} I(x, y, Z)$$

where M(Z) represents a focus metric, I(x,y,Z) represents an image intensity at given spatial coordinates (x,y,Z), $\bar{I}(Z)$ represents an average intensity in every pixel, and $N_{x,y}$ represents a total number of image pixels.

Software modules, that is, the defocused image calculation module 140 and the CD evaluation module 150, may be implemented by one or more processors executing one or more programs, such as any of Microsoft Visual Studio, Fortran, Borland C++ Builder, Matlap, Mathematica, Labview, and so forth, without being limited thereto.

Referring to FIGS. 1 and 2, the defocused image calculation module 140 may receive experimental conditions from the optical system parameter control module 110 and an OTF from the OTF measurement module 120. The defocused image calculation module 140 may theoretically calculate a defocused image of a sample, while taking into account the measured OTF and the specified experimental conditions. The calculation may be performed with respect to various CD values specified by the optical system parameter control module 110, and the calculated defocused images may be transmitted to the CD evaluation module 150.

Referring to FIGS. 1 and 2, the CD evaluation module 150 compares the experimentally measured (that is, registered) defocused image obtained from the optical module 130 with the calculated image obtained from the defocused image calculation module 140. This module for comparing the measured image with respect to the nanostructured surface of the sample with the calculated image is of particular importance to the measurement system. For comparison, the measured image obtained from the optical module 130 and a predetermined CD value variation range are considered, and the calculated image obtained from the defocused image calculation module 140 is transmitted for input to the CD evaluation module 150. The comparison results in an optimized estimate of the measured CD value and/or a narrower CD value variation range.

The calculation of the defocused image calculation module 140 and the comparison of the CD evaluation module 150 are repeated while changing the CD value, until the calculated image and the measured image match. The CD value that corresponds to a match between the calculated image and the measured image may represent the best estimate of the measured CD value of the nanostructured surface of the sample.

Figure 4:
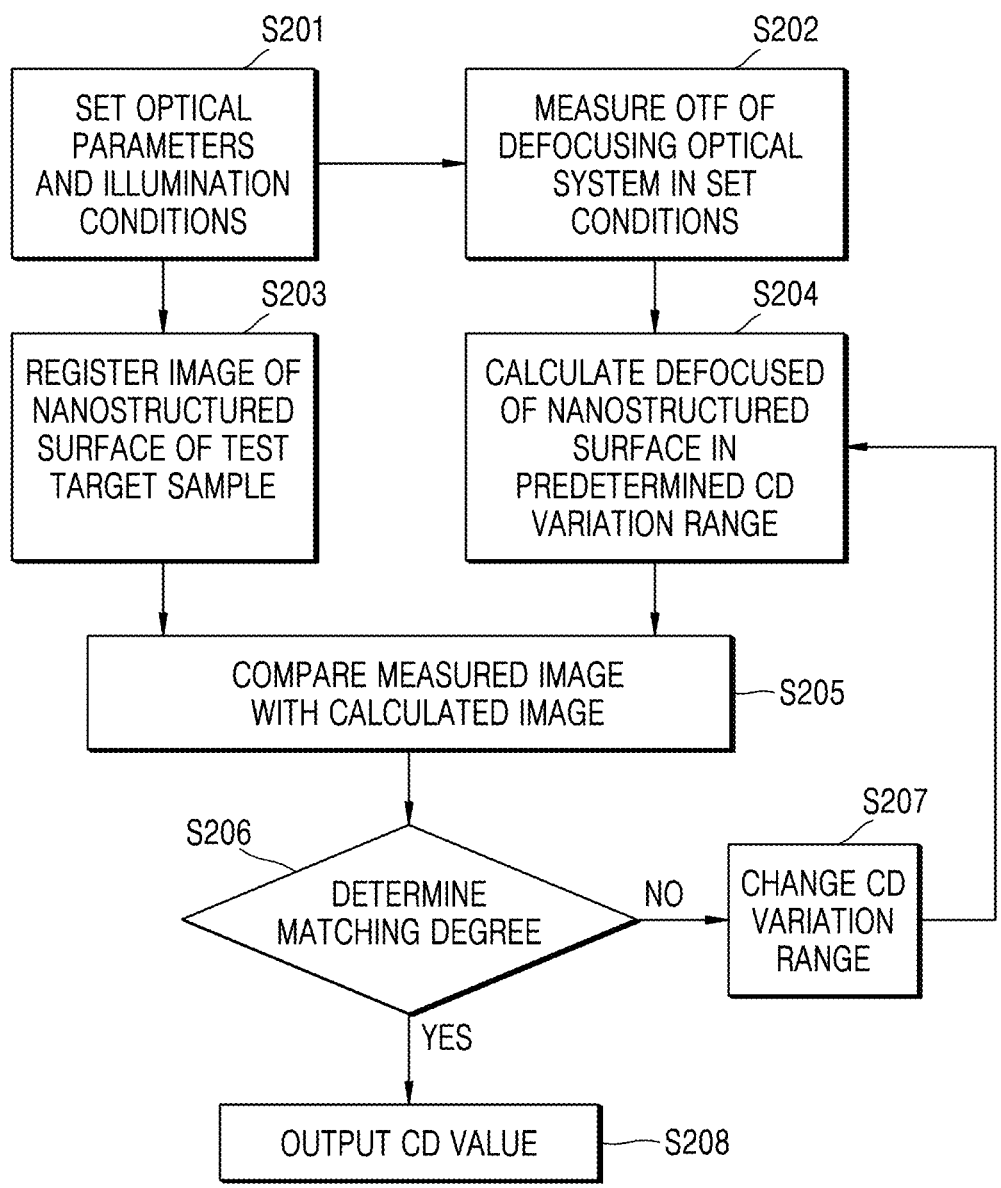
FIG. 4 illustrates a flowchart of operations of a measurement method, according to an exemplary embodiment.

FIG. 4 is a flowchart of a measurement method, according to an exemplary embodiment. Referring to FIG. 4, first, in operation S201, an optical system parameter and an illumination condition to be used by a microscope optical system in order to register an image of a nanostructured surface of a sample are set in operation S201. The optical system parameters may include parameters as described above with reference to FIGS. 1 and 2.

By using the microscope optical system as configured according to the optical system parameter and the illumination condition, a defocused image of the nanostructured surface is registered in operation S203. To register the defocused image, the sample 8 having the nanostructured surface as illustrated in FIG. 2 may be fitted by the precision mechanical stage 9.

With the set optical system parameter and illumination condition, the OTF of the defocusing optical system is measured in operation S202. By using the OTF as measured in a predetermined CD variation range, a defocused image of a nanostructured surface is calculated in operation S204. A software module for calculation is based on numerical solvers of Maxwell equations and may be implemented using any of the RCWA method and the FDTD method. Input parameters for calculation may include optical system parameters that are set to define illumination and nanostructured surface registration conditions and a CD value variation range. In an actual semiconductor manufacturing process, an approximate CD value variation range is well known, and may be defined according to an expert's opinion.

Next, the calculated image and the measured image are compared with each other in operation S205. The comparison results in an optimized estimate of the measured CD value and/or the narrower CD value variation range. Several methods for digital image comparison which are applicable to a software module for comparison are known from documents. For example, the comparison result may include a number that indicates a degree of matching between the measured image and the calculated image. A "focus metric" parameter, which is defined in order to analyze images that have different defocusing degrees, may be used.

The matching degree as between the calculated image and the measured image is determined in operation S206, and if the determined matching degree meets a predetermined minimum accuracy level, then a CD value that corresponds to a match is output as a measured C value in operation S208. If no match is achieved, i.e., the determined matching degree fails to satisfy the predetermined minimum accuracy level, then the CD value variation range is changed in operation S207, and operation S204 of calculating the image of the nanostructured surface of the sample and operation S205 of comparing the calculated image with the measured image may be repeated. According to a result of the comparison between the measured image and the calculated image, a narrower CD variation range may be defined.

There are various methods for comparing the measured image with calculated image in order to select a CD value. For example, any of an optimization technique and an image library calculation technique may be used. When the optimization technique is used, the best estimate of the CD value is obtained when an absolute value of a difference between the measured image and the calculated image is minimized. When the library calculation technique is used, the measured image may be compared in a stepwise manner with previously calculated images, based on an assumption that the CD value varies within a known range.

According to the above-described optical measurement system and method, one defocused image is measured for a nanostructured surface of a test target sample, and is compared with a calculated image in order to estimate a CD value. The one defocused image is an image that has a defocusing degree which varies based on a position, and thus a process of mechanically scanning a sample along a focus direction to obtain an image that has a different defocusing degree is not required, thus improving reliability, stability, and accuracy of measurements.

According to the above-described measurement system and method, CD values of periodical and non-periodical nanostructures may be measured.

The above-described optical measurement system and method for a measuring a CD of a nanostructure have been described with reference the illustrated exemplary embodiments, but these are merely an example, and it will be understood by those of ordinary skill in the art that various modifications and equivalent other embodiments are also possible. The disclosed exemplary embodiments should be considered in a descriptive sense rather than in a limiting sense. The scope of the disclosed exemplary embodiments is disclosed in the appended claims rather than the above description, and any difference in its equivalent range should be construed as being included in the disclosed exemplary embodiments.

What is claimed is:
1. An optical measurement system comprising:
an optical module comprising an optical system, and the optical module being configured to illuminate a sample and to register a defocused image of a nanostructured surface of the sample;
an optical system parameter control module configured to set at least one optical parameter of the optical system;
an optical transfer function (OTF) measurement module which is implemented by at least one processor and configured to measure an OTF;
a defocused image calculation module which is implemented by at least one processor and configured to calculate the defocused image based on the measured OTF and the at least one optical parameter; and a critical dimension (CD) evaluation module which is implemented by the at least one processor and configured to compare the registered defocused image with the calculated defocused image and to output a CD value of the nanostructured surface of the sample.

2. The optical measurement system of claim 1, wherein the OTF measurement module is further configured to analyze interferograms that correspond to an illumination light aberrated by the optical measurement system and a reference light.

3. The optical measurement system of claim 1, wherein the OTF measurement module is further configured to measure the OTF based on the registered defocused image of the nanostructured surface of the sample.

4. The optical measurement system of claim 1, wherein the optical system parameter control module is further configured to set at least one parameter of the optical measurement system and at least one parameter of the OTF measurement module, wherein the at least one parameter of the optical measurement system comprises at least one from among a spectrum and a polarization of a light source, a numerical aperture of an objective lens, a full range and a step size of defocusing of the sample, and a magnification of the optical measurement system.

5. The optical measurement system of claim 1, wherein the defocused image calculation module is further configured to calculate the image by using at least one of a Rigorous coupled-wave analysis (RCWA) method, a finite-difference time-domain (FDTD) method, a finite elements method (FEM), and a scattering matrix.

6. The optical measurement system of claim 1, wherein the CD evaluation module is further configured to find a defocused image that matches a registered defocused image from a defocused image library calculated in advance for different CD values.

7. The optical measurement system of claim 1, wherein when an accuracy of the output CD value of the nanostructured surface of the sample fails to satisfy a predetermined minimum accuracy, the defocused image calculation module is further configured to repeat an image calculation by using a smaller CD step size until the accuracy of the CD value satisfies the predetermined minimum accuracy.

8. The optical measurement system of claim 1, wherein the OTF measurement module is further configured to measure a phase factor of the OTF and to separately measure an amplitude factor of the OTF.

9. An optical measurement method comprising:
setting at least one optical parameter of the optical measurement system of claim 1;
measuring an optical transfer function (OTF) of the optical measurement system;
registering a defocused image of a nanostructured surface of a sample at at least one sample position along an optical axis of an optical system based on the optical measurement system;
calculating a defocused image based on the measured OTF in a preset critical dimension (CD) value range; and
evaluating an accuracy of a CD of the nanostructured surface of the sample by comparing the registered defocused image with the calculated defocused image.

10. The optical measurement method of claim 9, wherein the measuring the OTF comprises analyzing interferograms that correspond to an illumination light aberrated by the optical measurement system and a reference light.

11. The optical measurement method of claim 9, wherein the measuring the OTF comprises measuring the registered defocused image of the nanostructured surface of the sample.

12. The optical measurement method of claim 9, wherein the at least one parameter of the optical measurement system comprises at least one from among a spectrum and a polarization of a light source, a numerical aperture of an objective lens, a full range and a step size of defocusing of the sample, and a magnification of the optical measurement system.

13. The optical measurement method of claim 9, wherein the evaluating the accuracy of the CD is performed based on an arithmetic difference between the registered defocused image and the calculated defocused image as a measure of a CD value that corresponds to the nanostructured surface of the sample.

14. The optical measurement method of claim 9, wherein the evaluating the accuracy of the CD is performed based on a focus metric function as a measure of a CD value that corresponds to the nanostructured surface of the sample.

15. The optical measurement method of claim 9, wherein the evaluating the accuracy of the CD comprises finding a defocused image that matches a registered defocused image from a defocused image library calculated in advance for different CD values.

16. The optical measurement method of claim 9, wherein, when an accuracy of the output CD value of the nanostructured surface of the sample fails to satisfy a predetermined minimum accuracy, the calculating the defocused image is repeated by using a smaller CD step size, and
the evaluating the accuracy of the CD is repeated until the accuracy of the CD value satisfies the predetermined minimum accuracy.

17. The optical measurement method of claim 9, wherein the measuring the OTF comprises measuring a phase factor of the OTF and separately measuring an amplitude factor of the OTF.

* * * * *